(12) United States Patent
Armbruster et al.

(10) Patent No.: US 7,790,853 B2
(45) Date of Patent: Sep. 7, 2010

(54) DETERMINATION OF BONE-SIALOPROTEIN IN BODILY FLUIDS FOR ONCOLOGICAL PROBLEMS

(76) Inventors: Franz Paul Armbruster, Immundiagnostik AG, Wiesenstrasse 4, 64625 Bensheim (DE); Markus Karmatschek, c/o Immundiagnostik AG, Wiesenstrasse 4, 64625 Bensheim (DE); Mats Paulsson, Institut Fuer Biochemie, Medizinische Fakultaet, Universitaet zu Koeln, Joseph-Stelzmann-Str. 52, 50931 Cologne (DE)

(*) Notice: Subject to any disclaimer, the term of this patent is extended or adjusted under 35 U.S.C. 154(b) by 150 days.

(21) Appl. No.: 10/480,441

(22) PCT Filed: Jun. 6, 2002

(86) PCT No.: PCT/EP02/06219

§ 371 (c)(1),
(2), (4) Date: Jul. 26, 2004

(87) PCT Pub. No.: WO02/100901

PCT Pub. Date: Dec. 19, 2002

(65) Prior Publication Data

US 2005/0054016 A1    Mar. 10, 2005

(30) Foreign Application Priority Data

Jun. 13, 2001    (EP) .................................. 01114388

(51) Int. Cl.
*C07K 16/00*    (2006.01)
*G01N 33/53*    (2006.01)
*G01N 33/574*    (2006.01)

(52) U.S. Cl. .................. 530/387.1; 530/391.3; 435/7.1; 435/7.92; 435/7.23

(58) Field of Classification Search ........................ None
See application file for complete search history.

(56) References Cited

U.S. PATENT DOCUMENTS

| 5,340,934 A * | 8/1994 | Termine et al. ............. 536/23.5 |
| 6,407,213 B1 * | 6/2002 | Carter et al. ............. 530/387.3 |
| 2002/0025307 A1 * | 2/2002 | Koeneman et al. ....... 424/93.21 |

FOREIGN PATENT DOCUMENTS

| WO | WO 99 50666 A | 10/1999 |
| WO | WO 00 62065 A | 10/2000 |

OTHER PUBLICATIONS

Camenisch et al., FASEB, vol. 13, p. 81-88, 1999.*
Karmatschek et al., Clin Chem, vol. 43, p. 2076-2082, 1997.*
Diel et al., Clin Can Res, vol. 5, p. 3914-3919, 1999.*
Fisher and Termine et al., JBC, vol. 265, p. 2347-51, 1990.*
Diel et al., Clinical Cancer Res. vol. 5,p. 3914-3919, 1999.*
Wuttke et al., J Biol Chem. vol. 276, p. 36839-36848, 2001.*
P21815, sequence of human BSP.*
Karmatschek et al., Clinical Chemistry, vol. 43, No. 11, pp. 2076-2082 (1997).
Fisher et al., Acta Orthopaedica Scandinvica, vol. 66, No. Suppl 266, pp. 61-65 (1995).
Diel et al., Clinical Cancer Research, vol. 5, No. 12, pp. 3914-3919 (1999).
Waltregny et al., Journal of Bone and Mineral Research, vol. 15, No. 5, pp. 834-843 (2000).
Withold et al., Clinical Chemistry, vol. 43, No. 1, pp. 85-91 (1997).

* cited by examiner

*Primary Examiner*—Larry R. Helms
*Assistant Examiner*—Lei Yao
(74) *Attorney, Agent, or Firm*—Birch, Stewart, Kolasch & Birch, LLP

(57) ABSTRACT

The invention relates to antibodies or a plurality of antibodies against human bone sialoprotein (BSP), characterized in that the antibodies bind to epitopes which are present only in human bone sialoprotein from tumor cells, the post-translational glycosylation of which is modified or incomplete in the region of amino acids of 120 to 135, containing the amino acids TGLAA (SEQ ID NO: 2), in comparison with normal bone sialoprotein from bones. The antibodies are put to use in an immunoassay for the diagnosis and prognosis of tumor diseases, in particular the diagnosis and prognosis of bone metastases in the case of primary breast carcinoma.

6 Claims, 4 Drawing Sheets

Figure 1:
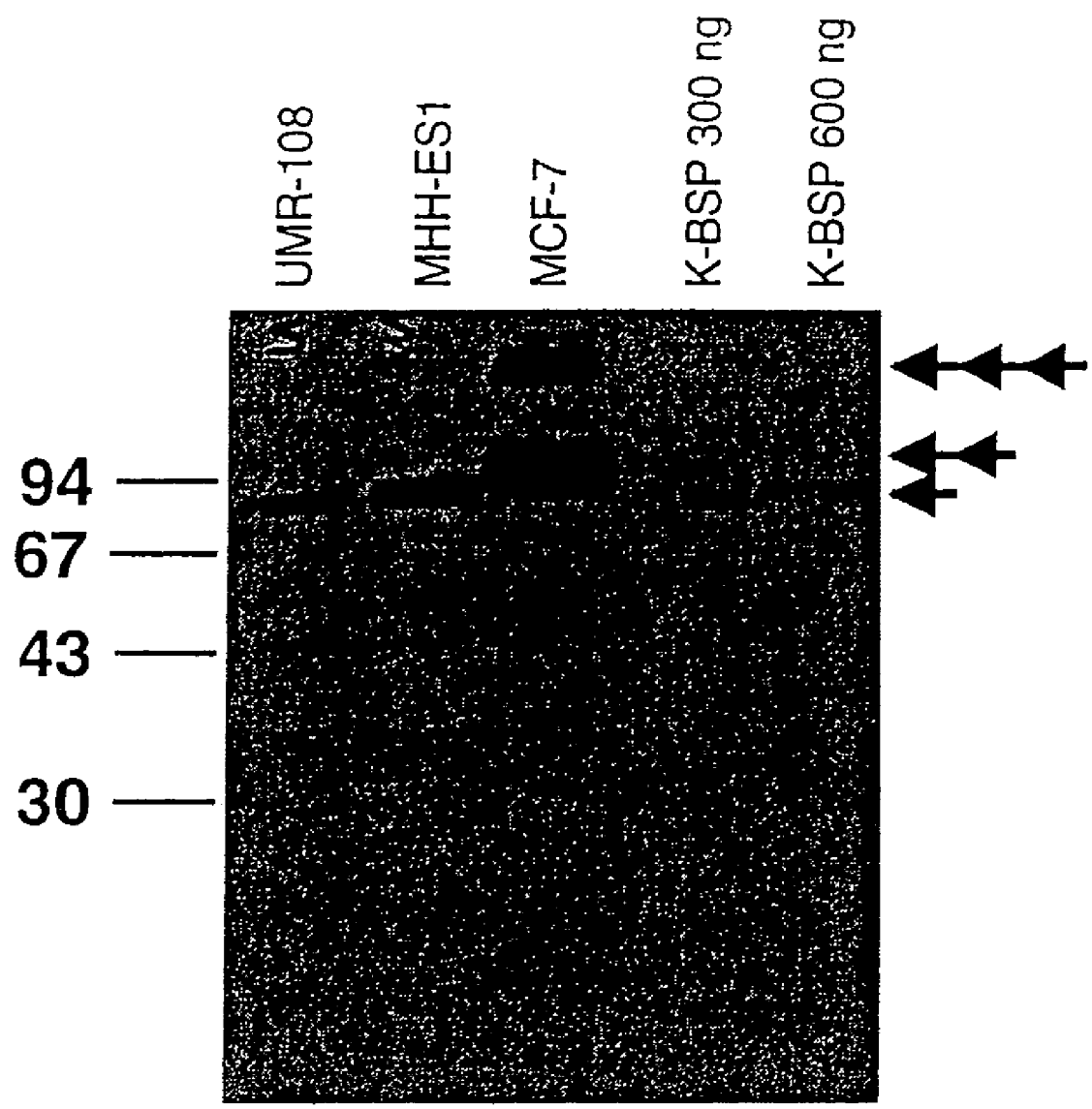

```
Phe-Ser-Met-Lys-Asn-Leu-His-Arg-Arg-Val¹⁰-Lys-Ile-Glu-Asp-Ser-
Glu-Glu-Asn-Gly-Val²⁰-Phe-Lys-Tyr-Arg-Pro-Arg-Tyr-Tyr-Leu-Tyr³⁰-
Lys-His-Ala-Tyr-Phe-Tyr-Pro-His-Leu-Lys⁴⁰-Arg-Phe-Pro-Val-Gln-
Gly-Ser-Ser-Asp-Ser⁵⁰-Ser-Glu-Glu-Asn-Gly-Asp-Asp-Ser-Ser-Glu⁶⁰-
Glu-Glu-Glu-Glu-Glu-Glu-Glu-Thr-Ser-Asn⁷⁰-Glu-Gly-Glu-Asn-Asn-
Glu-Glu-Ser-Asn-Glu⁸⁰-Asp-Glu-Asp-Ser-Glu-Ala-Glu-Asn-Thr-Thr⁹⁰-
Leu-Ser-Ala-Thr-Thr-Leu-Gly-Tyr-Gly-Glu¹⁰⁰-Asp-Ala-Thr-Pro-Gly-
Thr-Gly-Tyr-Thr-Gly¹¹⁰-Leu-Ala-Ala-Ile-Gln-Leu-Pro-Lys-Lys-Ala¹²⁰-
Gly-Asp-Ile-Thr-Asn-Lys-Ala-Thr-Lys-Glu¹³⁰-Lys-Glu-Ser-Asp-Glu-
Glu-Glu-Glu-Glu¹⁴⁰-Glu-Glu-Gly-Asn-Glu-Asn-Glu-Glu-Ser-Glu¹⁵⁰-
Ala-Glu-Val-Asp-Glu-Asn-Glu-Gln-Gly-Ile¹⁶⁰-Asn-Gly-Thr-Ser-Thr-
Asn-Ser-Thr-Glu-Ala¹⁷⁰-Glu-Asn-Gly-Asn-Gly-Ser-Ser-Gly-Gly-Asp¹⁸⁰-
Asn-Gly-Glu-Glu-Gly-Glu-Glu-Glu-Ser-Val¹⁹⁰-Thr-Gly-Ala-Asn-Ala-
Glu-Gly-Thr-Thr-Glu²⁰⁰-Thr-Gly-Gly-Gln-Gly-Lys-Gly-Thr-Ser-Lys²¹⁰-
Thr-Thr-Thr-Ser-Pro-Asn-Gly-Gly-Phe-Glu²²⁰-Pro-Thr-Thr-Pro-Pro-
Gln-Val-Tyr-Arg-Thr²³⁰-Thr-Ser-Pro-Pro-Phe-Gly-Lys-Thr-Thr-Thr²⁴⁰-
Val-Glu-Tyr-Glu-Gly-Glu-Tyr-Glu-Tyr-Thr²⁵⁰-Gly-Val-Asn-Glu-Tyr-
Asp-Asn-Gly-Tyr-Glu²⁶⁰-Ile-Tyr-Glu-Ser-Glu-Asn-Gly-Glu-Pro-Arg-
Gly-Asp-Asn-Tyr-Arg-Ala-Tyr-Glu-Asp-Glu²⁸⁰-Tyr-Ser-Tyr-Phe-Lys-
Gly-Gln-Gly-Tyr-Asp²⁹⁰-Gly-Tyr-Asp-Gly-Gln-Asn-Tyr-Tyr-His-His³⁰⁰-
Gln
```

Fig. 3

Aminoacid sequence of secreted BSP

Fig. 4

```
18 RIA                     bsp                    DATE  22.05.2002
TIME(MIN)     1.000        1251  16.0 /  84.0 (keV)   BOUND
CONSTANT/FACTOR 1.000      LOWER THR.  0.100      UPPER THR.  120.000 (ng/ml)

IDENT. #    CPM-1     CPM-1    AVG-CPM   %C.V.   %B/B0  DEL.

1  1  1  30790.3   30845.9   30818.1   0.13     TC
    3  1  3     71.5     107.3      92.9  27.74     NSB         %NSB/TC  0.3
    5  1  5   9819.1    9438.3    9632.4   2.80     B0          %B0/TC  31.0
    7  1  7   6030.6    5978.3    6004.6   0.62    61.97 1.87
    9  1  9   5354.3    5126.9    5243.1   3.07    53.99  3.7              }  Calibration Curve
   11  1 11   3832.8    3921.3    3877.6   1.61    39.87  7.5
   13  2  1   2944.5    3001.4    2973.2   1.35    30.20  15
   15  2  3   2114.5    2331.0    2228.0   6.88    22.38  30
   17  2  5   1944.7    1696.8    1829.2   9.60    18.20  60
   19  2  7   1257.1    1579.6    1436.7  15.99    14.09  H.V. 120
```

```
LINEAR CORRELATION COEFFICIENT = 0.9923

AUTOMATIC SELECTION OF FIT

LOGIT-LOG-REGRESSION:  LINEAR FIT              QUADR. FIT               CUBIC FIT

STANDARD-    RECALC.   PERCENT.        RECALC.   PERCENT.        RECALC.   PERCENT.
CONCENTR.    CONCENTR. DEVIATION       CONCENTR. DEVIATION       CONCENTR. DEVIATION 1.870      1.679     -10.22          2.075     10.95          2.000      6.95
   3.750      2.989     -20.30          3.234    -13.75          3.305    -11.85
   7.500      8.254      10.05          7.597      1.28          7.889      5.19
  15.000     17.220      14.79         15.209      1.39         15.241      1.60
  30.000     35.086      16.95         32.521      8.40         31.094      3.64
  60.000     55.289      -7.85         56.423     -5.96         53.724    -10.45
 120.000     94.475     -21.27        119.214     -0.65        142.061     18.38

GOODNESS OF FIT:    0.1810                  0.1024                 0.1505

QUADR. FIT SELECTED

SLOPE AT 50% B/B0    0.6972

ESTIMATED DOSES

20% B/B0 =   43.715(ng/ml)
 50% B/B0 =    4.053(ng/ml)
 80% B/B0 =    0.689(ng/ml)

MIN. CONC.    0.117(ng/ml)    =  95.6% B/B0
MAX. CONC.  479.938(ng/ml)    =   9.7% B/B0
```

DETERMINATION OF BONE-SIALOPROTEIN IN BODILY FLUIDS FOR ONCOLOGICAL PROBLEMS

The present application is a National Stage entry of International Application No. PCT/EP2002/06219 filed on Jun. 6, 2002, which claims priority under 35 U.S.C. §119(a)-(d) to European Patent Application 01114388.0 filed Jun. 13, 2001.

The invention relates to the immunological determination of bone sialoprotein (BSP) in body fluids, for the diagnosis and monitoring of diseases of the bone metabolism and bone structure and in particular for the diagnosis, prognosis, prophylaxis and therapy of bone metastases of primary carcinomas.

The bone sialoprotein (BSP) is a phosphorylated bone glycoprotein having a relative mass of ca. 80 kDa in the SDS-PAGE. The cDNA for BSP codes for a peptide sequence of ca. 33 kDa (Fisher L. W. et al. (1990), J. Biol. Chem. 265, 2347-51; U.S. Pat. No. 5,340,934). BSP is one the few matrix proteins the occurrence of which on mineralising tissue such as bones, dentin and calcifying cartilage is restricted. BSP represents ca. 10 to 15% if the total non-collagenic proteins in the bone matrix. It is as a rule expressed by cells which take part in the formation of dentin, bones and cartilage, for example osteoblasts, developing osteocytes, hypertrophic chondrocytes, odontoblasts and cementoblasts.

Alongside this, BSP is also formed by trophoblasts in the placenta and some types of cancer cells, e.g. in the case of lungs, breast, prostate, thyroid and neuroblastoma primary and secondary tumors, in the case of multiple myeloma and in bone metastases. The degree of expression of BSP by the tumor closely correlates with the severity of the cancer (Waltregny D. et al., *Increased expression of bone sialoprotein in bone metastases compared with visceral metastases in human breast and prostate cancers*, in J. Bone Miner. Res., 2000, 15(5), 834-43; Bellahcéne, A. et al., *Bone sialoprotein expression in primary human breast cancer is associated with bone metastases development*, in J. Bone Miner. Res., 1996, 11, 665-670; Waltregny, D. et al., *Prognostic value of bone sialoprotein expression in clinically localised human prostate cancer*, in Journal of the National Cancer Institute, 1998, 90, 1000-1008; Bellahcéne, A. et al., *Expression of bone sialoprotein in primary breast cancer is associated with poor survival*, in Int, J. Cancer, 1996, 69, 350-353).

For dentin, bones and cartilage, two functions are attributed to BSP. As an adhesion molecule, it is supposed to bring about attachment and dissemination of cells on the tissue matrix. Since in vitro it forms crystallisation nuclei for biological apatite it is suspected that in vivo it takes part in mineralisation. The switching off of the BSP gene in knockout mice leads to no recognisable disruption of the building and functioning of the skeleton.

In tumors BSP is attributed with participation in microcalcification (Castronovo, V. et al., *Evidence that breast cancer associated microcalcifications are mineralized malignant cells*, in Int. J. Oncol., 1998, 12, 305-308) and the colonisation of bones by metastasising tumor cells (Bellahcéne, A. et al., *Expression of bone sioloprotein in primary breast caner is associated with poor survival*, in Int. J. Cancer, 1996, 69, 350-353). The level of concentration of BSP in the serum of patients with primary carcinomas serves for diagnosis of whether these patients have bone metastases or such are likely to arise from the primary tumor (Diploma Thesis of Ms. Ina-Alexandra Meier, Development of a radioimmunoassay for the determination of bone sialoprotein (BSP) ["*Entwicklung eimes Radioimmunoassays zur Bestimmung von Bonesialoprotein (BSP)*]", 1996, Darmstadt, Technical University [Fachhochschule], Specialist Field Chemical Technology [FB Chemische Technologie]; Dissertation of Mr. Markus Karmatschek, Isolation of bone sialoprotein from human bones, Structure of a radioimmunoassay for the measurement thereof in serum ["*Isolierung von Bonesialoprotein aus humanem Kjiochen, Aufbau eines Radioimmunoassays zur dessen Messung im Serum"]*, 1996; Specialist Field of Biotechnology at the Technical University of Darmstadt [F B Biologie der Technischen Hochschule Darmstadt]; Diel I. J. et al., *Elevated bone sialoprotein in primary breast cancer patients is a potent marker for bone metastases*; in Proceedings of ASCO, 1998, 17, Abstract 461; Diel I. J. et al, *Serum bone sialoprotein in patients with primary breast cancer is a prognostic marker for subsequent bone metastasis*, in Clin. Cancer Res., 1999, 5, 3914-19; DE 198 13 633; DE 198 21 533; WO 99/50666).

According to recent hypotheses, BSP is supposed to protect the trophoblasts and BSP-producing tumors from attack by the immune system. Namely, BSP binds with high affinity the factor H of the complement system, which is known to restrict the alternative path of the complementlysis. Also, BSP can specifically bind to the integrin receptors on the cell surface through its own recognition sequence (arginine-glycine-aspartate, RGD). In the case of expression of BSP the tumor cells are then supposed to bind the factor H in the blood and in the tissue fluids to their cell surfaces, or concentrate it around them. Such a protection of BSP from the complement system of the blood of the mother is suspected also for the trophoblasts in the placenta (Fedarko N. S. et al. *Factor H binding of bone sialoprotein and osteopontin enables tumor cells evasion of complement-mediated attack*, in J. Biol. Chem., 200, 275, 16666-16672; WO 00/062065).

Further there is also suspected a function of BSP in angiogenesis. Along with the adhesion of osteoclasts and osteoblasts to the bone matrix—through the binding of the RGD recognition sequence in the matrix to the alpha(v)beta(3) integrin receptors on the cell wall—it is also observed that the adhesion, dissemination and orientation of the endothelial cells is probably mediated by BSP. Namely, blood vessel formation around a tumor occurs in parallel with the BSP expression in the tumor cells (Bellahcéne A et al., *Bone sialoprotein mediates human endothelial cell attachment and migration and promotes angiogenesis*, in Circ. Res. 2000, 86(8), 885-91).

BSP thus stands at the center of events in the formation of tumors and metastases. Thus, the binding of BSP via the RGD sequence to vitronectin or integrin receptors of tumor and epithelial cells can be restricted by antagonists (U.S. Pat. Nos. 6,069,158; 6,008,213; 5,849,865; van der Pluijm et al., *Bone Sialoprotein peptides are potent inhibitors of breast cancer cell adhesion to bone in vitro*, in Cancer Res., 1996, 56, 1948-1955). EP 1 084 719 A1 teaches a pharmaceutical composition having BSP as active substance for the support of the repair of damaged bone and connective tissue. WO 94/13310 teaches a composition having a BSP binding protein of *staphylococcus aureaus* as active ingredient. WO 00/36919 discloses regulatory elements for the purposive monitoring and suppression of the expression of ESP in tumor and connective tissue cells, which promote calcification.

Since in body fluids free BSP is bound by complement factor H with high affinity and the BSP can bind to various receptors, its determination is problematic. Thus, there have been produced in rabbits antibodies against various peptide partial structures of BSP (Fisher, L. W. et al., *Antisera and cDNA probes to human and certain animal model bone matrix noncollagenous proteins*. Acta Orthop Scand Suppl., 1995, 266, 61-655), against recombinant BSP (Stubbs J T 3rd

et al., *Charaterization of native and recombinant bone sialoprotein: delineation of the mineral-binding and cell adhesion domains and structural analysis of the RGD domain*. J. Bone Miner. Res. 1997 12(8), 1210-22), and against BSP isolated from bones, which antibodies failed to recognise any BSP in human serum. Only after separation of the serum proteins via SDS-PAGE can BSP be detected with these on Western Blots. The significantly larger factor H molecule of 150 kDa probably masks the smaller BSP (of ca. 65 kDa) to such an extent that antibodies cannot bind. Further, factor H is present in excess in the serum (0.5 mg factor H/mL in comparison to BSP with <20 ng/ml Serum in the case of healthy persons and max. 160 ng/ml in the case of tumor patients). It has been claimed that due to the binding with factor H immunological direct determination of BSP in body fluids is impossible, without reducing sample preparation (Fedarko N. S. et al., *Factor H binding of bone sialoprotein and osteopontin enables tumor cell evasion of complement-mediated attack*, in J. Biol. Chem., 200, 275, 16666-16672; WO 00/062065). Following our investigations, although such a sample preparation or protein splitting allows a quantitative determination of the BSP present in body fluids, the values obtained allow no answers to be given for oncological purposes.

It is the object of the invention to make available a method for the immunological determination of BSP in body fluids. It is in particular an object to make available a method for the direct determination of BSP in body fluids. It is a further object of the invention to make available antibodies against BSP for purposes in connection with the prognosis and diagnosis of a remote metastasisation of primary carcinomas in bones, for the diagnosis of bone metastases and for medical applications.

This object is achieved by means of antibodies according to claim 1 and their use for determination of BSP in body fluids. The antibodies against human bone sialoprotein (BSP) can in particular bind epitopes which are present on human bone sialoprotein from tumor cells, the post-translational glycosylation of which is modified or incomplete in the region of the amino acids 120 to 135 (SWISSPROT: SIAL_HUMAN, Acc. No. P21815, without signal sequence), containing the amino acids TGLAA (SEQ ID NO: 2), in comparison with normal bone sialoprotein from bones. They may be produced with a bone sialoprotein as antigen, preferably with a bone sialoprotein from tumor cells, which is modified in its glycosylation chemically or naturally. The bone sialoprotein modified in its glycosylation can also be produced by genetic engineering in tumor cells. It can also be produced against a peptidic antigen, including the amino acid TGLAA (SEQ ID NO: 2) or YTGLAA (SEQ ID NO: 3), if appropriate coupled to a carrier protein. In a further embodiment, the antibodies are produced by means of a bone sialoprotein, modified in its glycosylation, from bone material the donor of which was not capable of normal glycosylation of bone proteins. Due to their non-involvement in complement reactions, IgY antibodies of chicken are particularly preferred, in particular when these antibodies are human or humanised.

The antibodies in accordance with the invention can be put to use in a method for the determination of bone sialoprotein of tumor cells in body fluids, in particular in serum. In this manner a diagnosis and prognosis of bone metastases can be effected. The antibodies may of course also be used for diagnosis and if applicable for the production of a medicament, either as active ingredient—for example for prophylaxis and therapy of bone metastases or also as targeting means for the production of a diagnostic means or medicament.

A further object of the invention is diagnostic localisation of tumors and metastases by means of immune scintigraphy through the antibodies in accordance with the invention. Thereby the anti-BSP antibodies are radioactively marked and injected into the circulation of the patient. They bind specifically to tumors and metastases tissue and their distribution in the body can be pictorially represented then, e.g. by means of a scintiscanner.

For binding to the complex of factor H and BSP, the antibody must recognise epitopes of BSP which are not masked by the binding partner. The production of such antibodies has previously not been possible. The invention makes available such antibodies, because the antibodies are directed against an isoform of the folded bone sialoprotein (BSP) and bind to epitopes which are formed only by a folded bone sialoprotein from tumor cells, the glycosylations of which are modified or incomplete or missing in the region of the amino acids 120 to 135, including the amino acid sequence TGLAA (SEQ ID NO: 2) or YTGLAA (SEQ ID NO: 3), in comparison to the normal bone sialoprotein from bones. Normally there cannot be attained specific antibodies against post-translational or complex sugar structures on proteins, since such sugar structures are added in the same manner and form to many different proteins. Correspondingly, antibodies react against certain sugar structures with many different proteins and are then considered as a rule to be non-specific and of no value. This is different with bone sialoprotein from tumor cells. The altered or missing sugar structure brings about a different folding of the bone sialoprotein and creates new epitopes in which there are involved both amino acids or peptide structure and also the many remaining sugar residues. These epitopes are however characteristic for BSP from degenerate tumor cells.

Antibodies against these epitopes can be produced with a BSP, altered chemically or naturally in its glycosylation, as antigen and if applicable through purification or absorption to the isoform of the bone BSP. Preferably the antibodies are produced with the employment of BSP from tumor cells as antigen. Since BSP from tumor cells can be isolated in sufficient quantities only with difficulty, the genetically engineered expression of BSP modified in its glycosylation in tumor cells is the method of choice. It has also been found that some patients have in the bone material BSP modified in its glycosylation. This means that these patients, mostly very old and suffering from serious osteoporosis, produce a BSP which at least in part is not normally glycosylated. This BSP also is suitable in principle as an antigen for the obtaining of the antibodies in accordance with the invention. The isolation of the partially glycosylated isoform, which is comparable to the tumor isoform of the BSP, can be carried out analogously to described procedures (Karmatschek M et al., *Improved purification of human bone sialoprotein and development of a homologous radioimmunoassay*, in Clin. Chem. 1997, 43(11), 2076-82).

The antibodies can be produced in mice, guinea pigs, rabbits, dogs, goats, pigs, humans, donkeys or horses, but also in all mammals. Particularly preferred is the immunisation of birds, in particular chicken, since here due to the large evolutionary differences, antibodies against the tumor isoform of BSP can be obtained particularly easily. Further, the presence of IgY antibodies does not lead to an activation of the complement system, which could be problematic due to the possible binding between factor H and BSP. The antibodies in accordance with the invention recognise the tumor isoform of BSP in the bonding with factor H.

Thus, subjects of the invention are particular antibodies against the isoforms produced by tumors, and their use for antibody therapy or also for immune scintigraphy. As side effects, which are brought about by anti-BSP antibodies, there come in question: direct and indirect damage of the bones and dentin through activation of the immune system against the bone matrix and bone cells and/or direct destruction, in the employment of conjugates of the antibody with cell poisons or radioisotopes. Further, an immune scintigraphy is inconceivable with anti-BSP antibodies which bind to the bone matrix. The matrix would be radioactively marked and the localisation of tumors would be impossible.

The antibodies specific for human BSP are suitable for tumor therapy and localisation, since they do not bind or bind to only a slight extent to the bone matrix or to BSP producing cells of the skeleton and the dentin. In a particularly preferred application of the invention there are put to use for tumor therapy antibodies which are specific for tumor BSP and additionally recognise BSP in the complex with factor H. After application of such specific antibodies in tumor patients, free tumor BSP and tumor BSP bonded to factor H, in the blood and in tissue fluid, is neutralised and therewith the protection against complement activation removed, tumor cells specifically marked for destruction by the immune system (e.g. through classical activation of the complement cascade) and there are avoided side effects such as e.g. through activation of the immune system against the bone matrix or the dentin. In a further application of the invention human polyclonal Anti-BSP antibodies are isolated from the egg of transgenic chickens having humanised immune system.

Likewise suitable are monoclonal antibodies from the mouse or the chicken, which fulfil the above-described conditions and which can be obtained by means of screening. In a specific application of the patent there are employed for this purpose the monoclonal cell lines described by way of example. Further suitable are Fab fragments obtained through fragments of antibodies, e.g. proteolytically or by genetic engineering.

Particularly suitable are humanised poly- and monoclonal antibodies which recognise BSP in the complex with factor H and do not bind to BSP in the bone matrix. With the application of antibodies of the mouse and of the chicken there is however a particular therapeutic effect to be expected through formation of human anti-mouse antibodies (HAMA) or anti-chicken antibodies (HACA). HAMAs and HACAs can induce and strengthen an immune response of the organism to the tumor antigen. In the determination of tumor markers there arise, however, interferences with the HAMAs and HACAs which disrupt in vitro measuring methods. In this manner there are produced falsely high measurement values for tumor marker. This appears after immune scintigraphy or immune therapy with appropriate antibodies, so that a correct tumor marker determination in vitro can be effected only after absorption of the HAMAs or HACAs.

These effects can be suppressed through the employment of humanised antibodies. Polyclonal humanised anti-BSP antibodies can for example be obtained by immunisation of transgenic chickens with BSP, for which chickens in the embryonic stem cells the gene region for the chicken-specific Fc part of the immunoglobulin (IgY) is exchanged for a human specific one (U.S. Pat. No. 5,340,740; U.S. Pat. No. 5,656,479). The humanised antibodies are then deposited in eggs of the chickens and can be isolated from the egg yolk (Mohammed S. M. et al., Deposition of genetically engineered human antibodies into the egg yolk of hens. Immunotechnology, 1998, 4:115-125).

For the production of humanised monoclonal antibodies there may be obtained hybridoma cells of the mouse or the chicken with suitable anti-BSP antibodies, in accordance with standard methods, and from the genetic material contained in these cells humanised antibodies can be developed through recombination (U.S. Pat. No. 5,585,089; U.S. Pat. No. 5,565,332; U.S. Pat. No. 5,225,539; U.S. Pat. No. 5,693,761; U.S. Pat. No. 5,585,089; U.S. Pat. No. 5,530,101).

Figure 2:
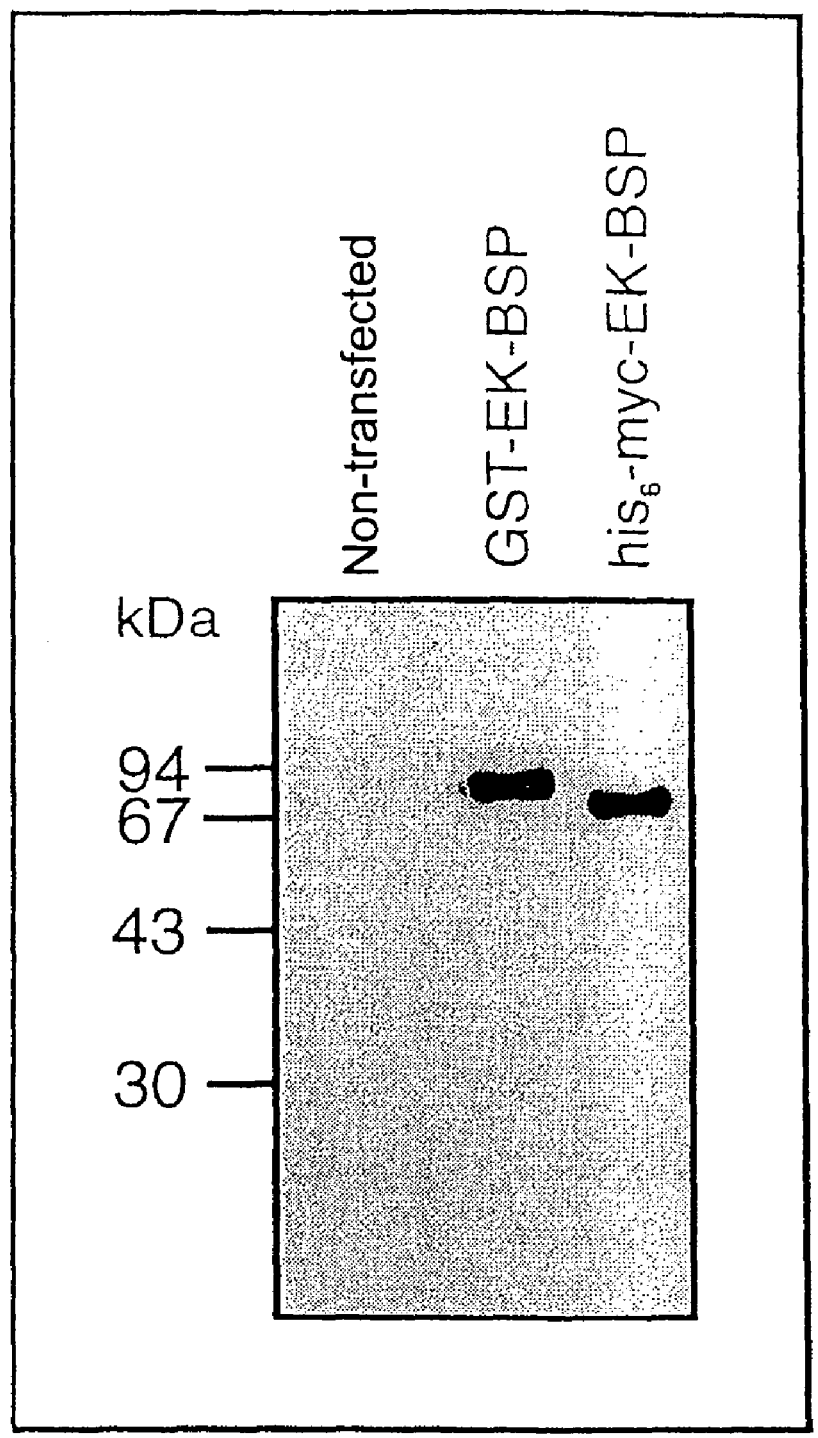

There will now be described further features and advantages of the invention with reference to the examples and the accompanying drawings. There is shown:

FIG. 1 a Western Blot with tumor and bone specific isoforms of BSP;

FIG. 2 a Western Blot of the cell culture supernatant of non-transfected EBNA-293 cells (negative control) and transfected EBNA-293 cells having the expression constructs GST-EK-BSP and his$_6$-myc-EK-BSP with the employment of a monoclonal mouse anti-BSP antibody;

FIG. 3 the amino acid sequence of secreted BSP (SEQ ID NO: 1) according to Fisher et al. (1991);

FIG. 4 an example of a computer printout for a measurement calibration curve.

EXAMPLE 1

Characterisation of Tumor and Bone Specific BSP Isoforms in Western Blot

Serum free supernatants of the human osteosarcoma cell lines UMR-108, MHH-ES 1 and of the breast cancer cell line MCF-7 (oestrogen receptor positive) and also of human BSP (K-BSP) purified from bones was separated by means of SDS-PAGE on a 10% gel under reducing and denaturing conditions and electrophoretically transferred to nitrocellulose. The membrane was incubated with the monoclonal mouse antibody. The detection of BSP was effected via an anti-mouse antibody of the goat coupled to peroxidase, and chemoluminescence detection on an X-ray film. The result is shown in FIG. 1. Molecular weight and path of the markers are indicated on the left side. The single and double arrowheads show the different behaviour of the bone/osteosarcoma BSP and MCF-7 BSP. The latter contains additionally a high molecular weight band (triple arrow) which is absent in the other tracks. BSP from one tumor cell line thus has a significantly higher molecular weight than BSP from bone and from osteosarcoma cell lines, whereby beyond this a second isoform with even higher molecular weight can be observed.

EXAMPLE 2

Production of Polyclonal Antibodies by Means of Immunisation of Chickens with Bone BSP and BSP Peptide Part Structures Chickens and rabbits were immunised with BSP which was isolated from patients in accordance with the procedure described by Karmatschek et al.

From the egg yolks and the sera, polyclonal immunoglobulins were isolated and tested for binding against various peptide part structures of BSP in an ELISA process. Table 1 shows the results of this epitope mapping. Thereby, peptide part structures of the overall 317 amino acids long peptide sequence of preproBSP (including leader sequences) were chemically synthesised and bound to a microtitration plate and the antibodies incubated on the plate. The test for binding was effected after incubation with a conjugate of peroxidase with anti-IgY immunoglobulins or anti-rabbit-IgG immunoglobulins and subsequent enzyme reaction through transformation of a chromogene as substrate.

TABLE 1

Epitope mapping of the obtained anti-BSP IgG and IgY (SEQ ID NOS: 4-10)

| Position of the peptide part structure in the BSP | Amino acid sequence | Reaction strength ELISA | |
|---|---|---|---|
| | | IgY | Rabbit IgG |
| 112-123 | LeuGlyTyrGlyGluAspAlaThrProGlyThrGly | − | ? |
| 216-227 | GluThrGlyGlyGlnGlyLysGlyThrSerLysThr | − | ? |
| 300-311 | PheLysGlyGlnGlyTyrAspGlyTyrAspGlyGln | − | ? |
| 130-144 | IleGlnLeuProLysLysAlaGlyAspIleThrAsnLysAlaThr | +/− | + |
| 124-138 | TyrThrGlyLeuAlaAlaIleGlnLeuProLysLysAlaGlyAsp | − | ++ |
| 137-151 | GlyAspIleThrAsnLysAlaThrLysGluLysGluLysGlu-SerAspGlu | − | + |
| 280-317 | SerGluAsnGlyGluProArgGlyAspAsnTyrArgAlaTyr-GluAspGluTyrSerTyrPheLysGlyGlnGlyTyrAspGly-TyrAspGlyGlnAsnTyrTyrHisHisGln | ++ | + |
| Human bone BSP | | +++ | +++ |

The results show that the obtained chicken antibodies preferentially bind to the C-terminal sequence of BSP, whereas the rabbit antibodies bind over a greater region.

Further, polyclonal antibodies (A0001) were obtained by means of immunisation of rabbits with the peptide structure TyrThrGlyLeuAlaAlaIleGlnLeuProLysLysAlaGlyAsp (SEQ ID NO: 11, position 124-138 of BSP) which preferentially react to this peptide part structure, but also specifically with human bone BSP.

Polyclonal antibodies (AK_tBSP), however, which were obtained through immunisation of rabbits with the peptide part structures ThrGlyLeuAlaAla (SEQ ID NO: 2) (position 125-130), for example TyrThrGlyLeuAlaAla (SEQ ID NO: 3) (position 124-130), that is after coupling to bovine thyroglobulin as carrier, react with the synthetic peptide part structure, but not with human bone BSP. These antibodies, surprisingly, recognize exclusively BSP from tumor cells.

For the investigations there were further employed the polyclonal antibodies A002 (obtained from L. W. Fisher) and A003 (obtained from Dr. van Ryden). These antibodies were obtained after immunisation with the peptide part structures
TyrGluSerGluAsnGlyGluProArg-GlyAspAsnTyrArgAlaTyrGluAsp (SEQ ID NO: 12) (A002)
Or
LeuLysArgPheProValGlnGlyGly (SEQ ID NO: 13).

The former peptide originated from the C-terminus of the BSP (positions 278-295) and contains the RGD (ArgGlyAsp) recognition sequence of the BSP for receptors of the integrin type. The latter peptide orginated from the N-terminus of the BSP primary structure. Also these peptides preferentially recognised the respective part structures and reacted specifically with human bone BSP.

EXAMPLE 3

Production of Recombinant BSP from Breast Cancer Cells, for Immunisation

From the plasmid B6-5g (Fisher L. W. et al., *Human bone sialoprotein. Deduced protein sequence and chromosomal localisation*, in J. Biol. Chem., 1990, 265(4), 2347-51) the complete cDNA for human BSP (without signal peptide) was amplified by means of PCR and cloned in the episomal eucaryotic expression vector pCEP-Pu (Kohfeldt E et al., *Properties of the extracellular calcium binding module of the proteoglycan testican*, in FEBS Lett. 1997, 414(3), 557-61). The primers were as follows:

Nhe I BSP (sense):
(SEQ ID NO: 14)
5' GCCCGCTAGCCTTCTCAATGAAAAATTTGCATCG-3'

Not I BSP (antisense):
(SEQ ID NO: 15)
5'-CAATGACTGCGGCCGCTCACTGGTGGTGGTAGTAATTC-3"

The Nhe I and Not I slicing sites introduced with the primers were necessary for the cloning in the expression vector PCEP-PU. This vector is moreover, for facilitating the protein purification, provided at the 5'-ends of the multiple cloning sites with various tags (e.g. His, Myc, G8T). These tags can be detached after purification of the protein with a protease (e.g. factor X or enterokinase) That the correct reading frame was kept to was checked by means of sequencing.

The expression constructs were introduced by means of liposome mediated stable transfection (FUGENE™ transfection reagent of the company Roche) inter alia into the following human cell lines:
the embryonic kidney cell line EBNA-293
the osteosarcoma cell lines SAOS-2 and MG-63
the human breast cancer cell line MCF-7.

A recombinant expression was obtained only in MCF-7 and EBNA-293 cells (see FIG. 2). The osteosarcoma cell lines did not express even after repeated transfection attempts.

EXAMPLE 4

Analysis of the Glycosylation of Recombinant BSP from Degenerate Cells and Bone BSP Transient cells were cultivated, 48 hours after transfection, for two days in serum-free medium. So that the proteins in the FCS did not make more difficult the purification of the recombinant BSP, BSP expressing cells were, after attainment of confluence, cultivated under serum free conditions. Under these conditions only EBNA-293 cells could survive longer than 2 to 4. The expression of the recombinant BSP was monitored through SDS-PAGE and immunoblots.

The investigation of serum-free cell culture supernatants yielded with all these cell lines a positive signal in the Western Blot, both with reference to BSP and also the presence of the various tags.

2.5 liter serum-free culture supernatant of the transfected MCF-7 cell line was purified via a nickel Sepharose™ column and there was obtained therefrom 250 µg homogeneous His-myc-EK-BSP. The so purified expression product was partially glyglosylated, however had no glycosylation at threonin 125, that is the threonin in the BSP sequence YT$^{125}$LPAA.

For the glycoanalysis the N-glycanes were enzymatically separated from the recombinant BSP (rBSP) or the bone BSP with the peptide N-glycosidase F (PNGase F, Roche). The enzyme brought about a cataylytic splitting of all N-glycane types from the asparagines. For the digestion, 20 to 200 µg BSP was precipitated with ethanol and the precipitant pellet incubated in 1% SDS, β-mercaptoethanol, 0.1 M EDTA for 30 minutes at room temperature with an excess of enzyme. There followed a digestion with N-glycosidase F overnight at 37° C. For de-salting the N-glycane solution the digestion was given via a 150 mg carbon column (carbograph SPE, Alltech) and the N-glycanes eluted with 25% aCN in 0.05% TFA.

The O-glycanes were sliced from the BSP by means of water-free hydrazinolysis using a kit (Oglycan release kit, Glyco). For this purpose, approximately 200 µg salt free BSP was lyophilised for 24 hours, had 50 µl hydrazine reagent added thereto under argon protective gas, dissolved and incubated for 5 hours at 60° C. The hydrazine was drawn off under vacuum. There followed a Re-N-acetylisation of the N-acetyl groups with acetic acid anhydrid.

The N- and O-glycanes were marked with the fluorescence dye 2-aminobenzamide (Fluka) and the 2-AB marked oligosaccharides digested sequentially with specific terminal glycosidases and analysed by means of MALDI-TOF mass spectrometry.

Discussion of the Analysis

The amino acid sequence of human BSP contains four potential N-glycosylation sites at the positions 88 (NTT), 161 (NGT), 166 (NST) und 174 (NGS). For O-glycosylation there is known no comparable consensus sequence. All identified N-glycane structures could be found both on the BSP isolated from bones and on the recombinant EBNA-293 BSP. There were however differences in the percentage proportion of the respective structures in the total N-glycanes. Thus, the main proportion of the BSP N-glycanes in bones was of triantenary structures (58%) and in the EBNA cell line of tetraantenary structures (48%).

For localisation of the O-glycosylation sites of recombinant BSP, the O-glycanes were removed by means of sequential digestion of the protein with neuraminidase, β-galactosidase and β-N-actylhexosaminidase, down to the core-GalNAc. The partially deglycosylated protein was then split by treatment with trypsin and V8 protease into peptide fragments. By means of MALDI-TOF mass spectrometry the masses of the peptides were determined and a part of the peptides sequenced by means of PSD-MALDI-TOF mass spectrometry. With this method, eight O-glycosylation sites of the recombinant BSP could be determined, 5 on the peptide 227-245 of SEQ ID NO: 1 (TTTSP . . . QVYR) and a maximum of 3 on the peptide between AS 120 and AS 135 having the sequence TGLAA (SEQ ID NO: 2). Of these, in the recombinant BSP, the threonines in the sequence DATPGTG (amino acids 117-123 of SEQ ID NO: 1) are O-glycosylated. With bone BSP there was effected a third O-glycosylation. With recombinant BSP no third glycosylation site is present. Probably, this gylcosylation site lies on the TGLAA (SEQ ID NO: 2)-BSP part structure.

EXAMPLE 5

Production of Anti-BSP IgY from Egg Yolks

For the purification of greater quantities of anti-BSP IgY for therapy and immune scintigraphy there are described various processes. The process of Akita and Nakai (Akita E. M. et al., Comparison of four purification methods for the production of immunoglobulins from eggs laid by hens immunised with an enterotoxigenetic E. coli strain, in J Immunol Methods. 1993, 160(2), 207-14) is preferentially used.

For the egg production there is used a highly productive species such as "Lohmann White" or "Lohmann Brown" with a productivity of 4.5 eggs per week and a production of over 10 mg specific IgY per yolk. The immunisation was effected with BSP antigen isolated from human bones, or recombinant, in Freund's Adjuvant, whereby after a basic immunisation with ca. 0.1 mg BSP, booster injections where given every Six weeks. Normally ca. 30% of these chickens do not react to the immunisation. The eggs were externally disinfected with peracetic acid, then broken and yolk separated from egg white. The yolks were then whisked with 5 to 10 times volume ice cold distilled water between pH 5 and 5.2 and incubated at 2 to 5° C. over 2 to 6 hours. Thereby there sediments out the yolk granulata which are substantially of lipoproteins. The aqueous supernatant was then filtered clear through filter paper (e.g. Whatman No. 1).

From this supernatant, the anti-BSP IgY can be homogenously purified directly or via affinity chromatography. There was chemically covalently bonded, through a Sepharose 4B column, activated with cyanogen bromide, BSP isolated from human bones or from culture supernatants of recombinant human cell lines. For bonding 1 g IgY there is needed 0.5 g immobilised BSP (covalently bonded to ca. 5 ml Sepharose™).

The bonded IgY is eluted via an acid gradient and thereafter the solution neutralised. This solution must then be desalted and the antibodies concentrated, which is possible on an large scale in the crossflow method (e.g. Amicon™, spiral filter SY 100 with a yield of 100,000 Dalton).

EXAMPLE 6

Isolation of anti-BSP IgY which is Bonded to the BSP Factor H Complex

The slight reaction of the polyclonal chicken antibody with BSP in the bone matrix can be excluded through selection of those antibodies which react with BSP in the complex with factor H. For this purpose there is chemically covalently bonded through cyanogen bromide activated Sepharose 4B either factor H or BSP isolated from bones or genetically engineered, and thereafter so much BSP or factor H applied to the column and bonded that all ligands in the matrix are complexed with the partner. Filtered yolk extract is then applied to this affinity column and as in Example 4 there is now obtained that fraction of antibodies which specifically bonds to the free epitope in the BSP-factor H complex.

EXAMPLE 7

Production of Human Anti-BSP Antibodies in Transgenic Chickens

Anti-BSP IgY has in human therapy or diagnosis some weaknesses. Some side effects such as foreign protein reactions are to be expected and the biological half-life amounts in comparison to human antibodies only to 12 to 24 hours. IgY does not activate the complement system.

Human antibodies against BSP can be produced in particular transgenic chickens, in which by means of gene targeting the constant region for avian immunoglobulin in the genes responsible for antibody formation has been exchanged by the constant region for human immunoglobulin. Suitable chicken stem cells and vector systems are described in U.S. Pat. Nos. 5,340,740, 5,656,479 and 5,464,764. After immunisation with BSP, such chickens react with the production of human antibodies in the egg.

EXAMPLE 8

Immunoblot Analysis of the Expression of BSP in Human Breast Cancer Cell Lines

The tumor cell lines MDA-MB-231 (breast cancer cell line, oestrogen receptor negative) MCF-7 (breast cancer cell line, oestrogen receptor positive) and T-47-D (breast cancer cell line, oestrogen receptor positive) were extracted with immune precipitation buffer and BSP precipitated with the polyclonal antibody mixture A0001 of rabbits against human BSP. The precipitates were applied, after denaturing, to SDS gels, the electrophoresis was carried out and the proteins transferred to nitrocellulose membranes. Thereafter there followed an immune colouring with the anti-BSP rabbit antiserum A001 and a monoclonal mouse-anti-BSP antibody (BSP 1.2), whereby there was employed as second antibody peroxydase conjugates of antibodies of the goat against rabbit IgG and against mouse IgG. In both blots A and B the bands of the immune precipitated BSP can be clearly recognized at 70000 Dalton.

In order to show the presence or absence of BSP on the cell surface of tumor cells, the cell surfaces of the breast cancer cell lines MDA-MB-231 and MCF-7 were biotinylated, extracted with immune precipitation buffer and BSP precipitated with the polyclonal antibody mixture A0001 of the rabbit against human BSP. The precipitates were, after denaturing, applied to SDS gels, the electrophoresis carried out and the proteins applied to a nitrocellulose membrane. Biotinylated proteins on this membrane were then demonstrated with a conjugate of peroxydase and streptavidine with the ECL system (Amersham).

EXAMPLE 8a

Expression of BSP in and on Breast Cancer Cell Lines

Human breast cancer cells of the lines T-47-D and MDA-MB-231 were marked immunofluorescently, both with and without prior permeablisation, with an anti-pig-BSP antibody from rabbit and an anti-rabbit antibody of the goat conjugated with fluorescene. Fluorescently marked BSP can be recognised in both cell lines after permeablisation. Only in the T-47-D cells could BSP be demonstrated by immunofluorescence also without permeabalisation.

EXAMPLE 9

Detection of BSP Expression in Tumor Cells via RT-PCR

From the tumor cell lines MDA-MB-231 (breast cancer cell line, oestrogen receptor negative), MCF-7 (breast cancer cell line, oestrogen receptor positive) and T-47-D (breast cancer cell line, oestrogen receptor positive) and human fibroblasts (HGF) as control cells, there was isolated mRNA, by reverse transcriptase the complementary cDNA was produced, and the BSP-cDNA amplified by means of PCR with BSP specific primers. The expression of BSP-mRNA was particularly high in the breast cancer cell line MCF-7, slight in the case of the MDA-MB-231 and T-47-D cells and not detectable in the control cell line.

EXAMPLE 10

Production of Humanised Monoclonal Antibodies

The monoclonal antibody BSP 1.2 can, due to its specific binding to tumor BSP, be put to use for the therapy of primary tumors and metastases. Thereby, the antibody binds on BSP on the cell surface of certain tumor cells and stimulates the immune system to destroy the cells, e.g. via the activation of the complement cascade. Similarly, there can be put to use also the polyclonal or monoclonal anti-BSP IgY for therapy. When this antibody is used, the human immune system reacts with the formation of its own antibodies—human anti-mouse-IgG antibodies (HAMAs) or human anti-chicken-IgY antibodies (HACAs). HAMAs and HACAs can induce or strengthen an immune response of the organism to the tumor antigen. In the determination of tumor markers there arises, however, interferences with the HAMAs and HACAs which disrupt in vitro measurement methods. In this way there arises falsely high measurement values for tumor marker.

Thus, humanised monoclonal antibodies are particularly suitable for the therapy and immune scintigraphy. A plurality of methods have been described how one derives appropriately humanised antibodies from the hybridoma cell lines, which produce monoclonal anti-BSP antibodies.

EXAMPLE 11

Conjugates of Anti-BSP Antibodies with Cell Poisons and Radioisotopes

In a further application of the invention there may be chemically covalently bonded with the anti-BSP antibodies or their Fab fragments cell poisons and radioisotopes. Antibodies marked with radioisotopes such as iodine 125 or iodine 131 are suitable with the application of smaller quantities for tumor localisation via immune scintigraphy and with the application of greater quantities for the direct destruction of the tumors. Such chemical conjugates can be produced for example by iodisation of the antibody with iodine 125 or 131 (Garvey, J. S et al., Methods in Immunology. $3^{rd}$ ed., W. A. Benjamin Publ., 177, 171-182). An overview of suitable methods for radio immune therapy and immune scintigraphy is found in Vuillez, Radioimmunotargeting: diagnosis and therapeutic use, in Bull Cancer. 2000, 87(11), 813-27.

EXAMPLE 12

Therapy of Tumors with Expression of BSP on the Cell Surface

It was first determined from biopsy material whether BSP was expressed on the surface of the tumor cells. Patients for whom BSP can be detected on the surface of the tumor cells can be considered for therapy with anti-BSP antibodies of the chicken, the mouse, the correspondingly humanised antibodies and with conjugates of these antibodies with cell poisons or radioisotopes.

The treatment of tumors with therapeutic antibodies which are directed against tumor markers expressed on the cell surface is state of the art. Thus, with the humanised antibody herceptin, against the receptor for the human epithelial growth factor, breast cancer can be successfully treated, even in the metastasising form, in ca. 25% of those affected (Hotaling T E et al., The humanized anti-HER2 antibody rhuMAb HER2 mediates antibody dependent cell-mediated cytotoxicity via FcgR III [abstract]. Proc Annu Meet Am Assoc Cancer Res 1996; 37:47; Pegram M D et al., Antibody dependent cell-mediated cytotoxicity in breast cancer patients in Phase III clinical trials of a humanized anti-HER2 antibody [abstract]. Proc Am Assoc Cancer Res 1997; 38:602.

Similarly as with herceptin, the appropriate anti-BSP antibody can be applied as an infusion, e.g. as a 90 minute infusion in the first application and later as a 30 minute infusion. The frequency of the infusions and the quantity of the antibodies are determined in accordance with the half-life of the antibodies in the blood (ca. 6 days with a humanised antibody and less than 24 hours with a chicken antibody) and the body weight.

EXAMPLE 13

Therapy of Tumors by Means of Neutralisation of Free BSP, not Bonded to Cells, and of the BSP-Factor H Complex With the methods described above it was determined whether the tumor cells of the patient express BSP which cannot be detected on the cell surface. In the case of these tumors it can be assumed that the cells give out BSP into the blood or the tissue fluid and e.g. through binding of factor H use this for the inactivation of the alternative path of the complement cascade or for migration into bone tissues. A further possible indicator for this tumor type are increased concentrations of the BSP in the blood serum (>20 ng/mL serum). In these cases anti-BSP antibodies can be put to use for the neutralisation of the free tumor BSP or the tumor BSP in complexes with factor H. The dose can then be set with regard to the quantity of the BSP present free in the serum and in the tissue fluid. For the therapy, there can be considered anti-BSP antibodies of the chicken, of the mouse and humanised anti-BSP antibodies, which can recognize the free BSP epitope in the complex with factor H. There can also be considered Fab fragments of these antibodies, which can be prepared in accordance with a standard procedure by means of proteolytic digestion (Garvey, J. S et al., Methods in Immunology. $3^{rd}$ ed., W. A. Benjamin Publ., 1977, 256-266). Also genetically engineered Fab fragments, derived from the above anti-BSP antibodies, come into consideration for such a therapy.

The invention thus makes available antibodies against the human bone sialoprotein (hBSP) which bind specifically only epitopes of hBSP of tumor cells, since tumor hBSP contains no post-translational O-glycosylation in the region of the amino acids 120 to 135 (SWISSPROT: SIAL_HUMAN, Acc. No. P21815, without signal sequence) containing the amino acids TGLAA (SEQ ID NO: 2). Differently from the normal hBSP from bones. The antibodies can recognize tumorgenic serum hBSP in the complex with the complement factor H and thus constitute a diagnostic and therapeutically valuable instrument.

EXAMPLE 14

RIA Measurement Series on Sera of Dialysis and Prostate Patients

The antibodies in accordance with the invention were put to use as trapper antibodies in ELISAs and in comparative measurement series the quantity of BSP in the serum of dialysis patients ("normal" BSP) and prostate patients with individually strongly increased BSP values of tumor origin were investigated.

The serum concentrations of human bone sialoprotein were investigated with polyclonal antibodies in accordance with the invention, of chicken, which also bind to epitopes which are present on human bone sialoprotein from tumor cells or strongly affected tissues due to the illness, that is on a human BSP the post-translational glycosylation of which is modified or incomplete in the region of the amino acids 120 to 135, including the amino acids TGLAA, in comparison with normal bone sialoprotein from healthy bones. As a rule 100 μl of the antibody solution was mixed with 125I-marked bone sialoprotein. After 24 hour incubation at 4° C., 100 μL solution of a second antibody were added (donkey-anti-chicken-IgG) and after 2 hours incubation at 4° C. the reaction mixture was centrifuged at 2000 G and the supernatant removed. After washing with 250 μL in PBS and a subsequent centrifuging (10 min at 2000G) the supernatant was again removed and the radioactivity of the pellets after addition of a counter fluid determined for 1 minute with a gamma-counter.

The necessary calibration curve was produced in the normal way, in this case with the aid of a 4-parameter curve algorithm. The standard values contained as a rule 0, 1.9, 3.8, 7.5, 15, 30, 60 and 120 μg/L BSP. The evaluation of the analytical accuracy through the addition of calibrators to the patient samples yielded as a mean a recovery in the range of over 99%. The computer printout for an example calibration curve is shown in FIG. 4.

The tabular measurement series below show that with the aid of the antibodies in accordance with the invention there can be reliably determined tumor and non-modified BSP in the serum of patients, quantitatively, and this in the presence of factor H and independently of the specific disease symptoms of the patients. A difficult and error prone separation of the serum proteins such as factor H from BSP is not necessary. In particular BSP from tumor cells can be reliably determined, which brings with it significant advances in the prognosis and the characterisation of the primary tumors and possible metastases.

TABLE 2

Measurement series of serum of patients with prostate carcinoma

| Box 1-4 | ID-No: Sialo | Sample No. | Code | Diagn | Sample volumes | Sialoprotein (ig/L) |
|---|---|---|---|---|---|---|
| 1 | 1 | 182 | E096 | 7 | | 81.2 |
| 1 | 2 | 183 | E162 | 7 | | 479.0 |
| 1 | 3 | 184 | E278 | 7 | | 28.0 |

TABLE 2-continued

Measurement series of serum of patients with prostate carcinoma

| Box 1-4 | ID-No: Sialo | Sample No. | Code | Diagn | Sample volumes | Sialoprotein (ig/L) |
|---|---|---|---|---|---|---|
| 1 | 4 | 185 | E476 | 7 | | 10.8 |
| 1 | 5 | 186 | E416 | 7 | | 38.5 |
| 1 | 6 | 187 | E560 | 7 | | 3.9 |
| 1 | 7 | 188 | H180 | 7 | | 30.2 |
| 1 | 8 | 189 | E653 | 7 | | 344.7 |
| 1 | 9 | 190 | D268 | 7 | | 112.3 |
| 1 | 10 | 191 | E527 | 7 | | 17.4 |
| 1 | 11 | 192 | E524 | 7 | | 18.5 |
| 1 | 12 | 193 | E441 | 7 | | 72.2 |
| 1 | 13 | 194 | H096 | 7 | | 251.0 |
| 1 | 14 | 195 | E824 | 7 | | 33.4 |
| 1 | 15 | 196 | E971 | 7 | | measurement ranges |
| 1 | 16 | 197 | D411 | 7 | | 10.9 |
| 1 | 17 | 198 | H601 | 7 | | 41.1 |
| 1 | 18 | 199 | H567 | 7 | 130iL | measurement ranges |
| 1 | 19 | 272 | H280 | 7 | | 31.5 |
| 1 | 20 | 273 | H316 | 7 | | |
| 1 | 21 | 274 | H420 | 7 | | 238.9 |
| 1 | 22 | 275 | I006 | 7 | | 17.9 |
| 1 | 23 | 276 | I007 | 7 | | 88.0 |
| 1 | 24 | 277 | I033 | 7 | | 27.2 |
| 1 | 25 | 278 | I084 | 7 | | 80.2 |
| 1 | 26 | 279 | I093 | 7 | | 29.1 |
| 1 | 27 | 280 | I142 | 7 | | 447.0 |
| 1 | 28 | 281 | 9407(Mü) | 7 | | 252.0 |
| 1 | 29 | 282 | 9245(Mü) | 7 | | 37.3 |
| 1 | 30 | 283 | 8940(Mü) | 7 | 250iL | 102.9 |
| 1 | 31 | 284 | 8779(Mü) | 7 | | |
| 1 | 32 | 285 | 8712(Mü) | 7 | | 11.9 |
| 1 | 33 | 286 | 8689(Mü) | 7 | | 7.4 |
| 1 | 34 | 287 | 8400(Mü) | 7 | | 32.7 |
| 1 | 35 | 288 | 8388(Mü) | 7 | | 30.8 |
| 1 | 36 | 289 | 8279(Mü) | 7 | | |
| 1 | 37 | 290 | H125 | 7 | | measurement ranges |
| 1 | 38 | 291 | H172 | 7 | | 9.0 |
| 1 | 39 | 292 | H180 | 7 | | — |
| 1 | 40 | 293 | H487 | 7 | | 5.9 |
| 1 | 41 | 104 | F968 | 4 | | 3.2 |
| 1 | 42 | 105 | F965 | 4 | | 76.7 |
| 1 | 43 | 106 | F923 | 4 | | 8.4 |
| 1 | 44 | 107 | F908 | 4 | | 11.1 |
| 1 | 45 | 108 | F821 | 4 | | 17.7 |
| 1 | 46 | 109 | F836 | 4 | | 3.5 |
| 1 | 47 | 110 | F342 | 4 | | 3.0 |
| 1 | 48 | 111 | F214 | 4 | | 8.4 |
| 1 | 49 | 112 | G843 | 4 | | 6.7 |
| 1 | 50 | 113 | G777 | 4 | | 10.9 |
| 1 | 51 | 114 | G753 | 4 | | 6.8 |
| 1 | 52 | 115 | G381 | 4 | | 3.1 |
| 1 | 53 | 116 | G984 | 4 | | 32.1 |
| 1 | 54 | 117 | G891 | 4 | | 17.0 |
| 1 | 55 | 118 | F196 | 4 | | 3.4 |
| 1 | 56 | 119 | F183 | 4 | | 6.9 |
| 1 | 57 | 120 | G010 | 4 | | 20.6 |
| 1 | 58 | 121 | F453 | 4 | | 6.0 |
| 1 | 59 | 122 | F640 | 4 | | 2.6 |
| 1 | 60 | 123 | G462 | 4 | | 10.7 |
| 1 | 61 | 124 | F423 | 4 | | 4.7 |
| 1 | 62 | 125 | F360 | 4 | | 3.0 |
| 1 | 63 | 126 | F875 | 4 | | 7.5 |
| 2 | 64 | 127 | G798 | 4 | | 8.9 |
| 2 | 65 | 128 | G786 | 4 | | 4.9 |
| 2 | 66 | 129 | G384 | 4 | | 8.2 |
| 2 | 67 | 130 | F529 | 4 | | 7.1 |
| 2 | 68 | 131 | E405 | 4 | | 1.3 |
| 2 | 69 | 132 | E419 | 4 | | |
| 2 | 70 | 133 | E274 | 4 | | 17.2 |
| 2 | 71 | 134 | E545 | 4 | | 6.3 |
| 2 | 72 | 135 | E166 | 4 | | 14.5 |
| 2 | 73 | 136 | F601 | 4 | | 8.0 |
| 2 | 74 | 137 | G432 | 4 | | 5.3 |
| 2 | 75 | 138 | F264 | 4 | | 4.5 |
| 2 | 76 | 139 | D297 | 4 | | |
| 2 | 77 | 140 | E355 | 4 | 180iL | 8.9 |
| 2 | 78 | 141 | E950 | 4 | | 10.0 |
| 2 | 79 | 142 | E391 | 4 | | 8.3 |
| 2 | 80 | 69 | F053 | 3 | | 11.0 |
| 2 | 81 | 70 | F177 | 3 | | 6.5 |
| 2 | 82 | 71 | F068 | 3 | | 8.0 |
| 2 | 83 | 72 | F237 | 3 | | 3.6 |
| 2 | 84 | 73 | F255 | 3 | | 7.5 |
| 2 | 85 | 74 | F378 | 3 | | 2.1 |
| 2 | 86 | 75 | F471 | 3 | | 7.5 |
| 2 | 87 | 76 | F484 | 3 | | 6.0 |
| 2 | 88 | 77 | F555 | 3 | | 12.5 |
| 2 | 89 | 78 | F281 | 3 | | 7.0 |
| 2 | 90 | 79 | F287 | 3 | | 4.0 |
| 2 | 91 | 80 | F372 | 3 | | 3.8 |
| 2 | 92 | 81 | F496 | 3 | | |
| 2 | 93 | 82 | F536 | 3 | | 4.2 |
| 2 | 94 | 83 | F561 | 3 | | 9.9 |
| 2 | 95 | 84 | F573 | 3 | | |
| 2 | 96 | 85 | F604 | 3 | | 6.6 |
| 2 | 97 | 86 | F651 | 3 | | 5.4 |
| 2 | 98 | 87 | F689 | 3 | | 1.7 |
| 2 | 99 | 88 | F695 | 3 | | 5.7 |
| 2 | 100 | 89 | F728 | 3 | | 8.8 |
| 2 | 101 | 90 | F785 | 3 | 200iL | 3.0 |
| 2 | 102 | 91 | F797 | 3 | | 5.3 |
| 2 | 103 | 92 | F824 | 3 | | 3.3 |
| 2 | 104 | 93 | F005 | 3 | 220iL | 2.6 |
| 2 | 105 | 94 | F017 | 3 | | 3.0 |
| 2 | 106 | 95 | F866 | 3 | | 6.3 |
| 2 | 107 | 96 | F881 | 3 | | |
| 2 | 108 | 97 | F890 | 3 | | 6.7 |
| 2 | 109 | 98 | F935 | 3 | | 5.7 |
| 2 | 110 | 99 | F944 | 3 | | 6.7 |
| 2 | 111 | 100 | F947 | 3 | | 8.0 |
| 2 | 112 | 101 | F950 | 3 | | |
| 2 | 113 | 102 | F983 | 3 | | 8.9 |
| 2 | 114 | 103 | F986 | 3 | | 5.7 |
| 2 | 115 | 1 | H128 | 1 | | 5.2 |
| 2 | 116 | 2 | H073 | 1 | | 8.9 |
| 2 | 117 | 3 | H072 | 1 | | 18.8 |
| 2 | 118 | 4 | H131 | 1 | | 6.9 |
| 2 | 119 | 5 | H082 | 1 | | 5.3 |
| 2 | 120 | 6 | H052 | 1 | | 3.2 |
| 2 | 121 | 7 | H057 | 1 | 120iL | 5.2 |
| 3 | 122 | 8 | H060 | 1 | | 2.7 |
| 3 | 123 | 9 | H061 | 1 | | 2.7 |
| 3 | 124 | 10 | H062 | 1 | | 2.0 |
| 3 | 125 | 11 | H063 | 1 | | 3.0 |
| 3 | 126 | 12 | H065 | 1 | | 4.3 |
| 3 | 127 | 13 | H067 | 1 | | 3.9 |
| 3 | 128 | 14 | H070 | 1 | 120iL | 4.3 |
| 3 | 129 | 15 | H097 | 1 | | 3.8 |
| 3 | 130 | 16 | H116 | 1 | 220iL | 11.0 |
| 3 | 131 | 17 | H134 | 1 | | 3.9 |
| 3 | 132 | 18 | H139 | 1 | | 3.7 |
| 3 | 133 | 19 | H140 | 1 | | 12.1 |
| 3 | 134 | 20 | H143 | 1 | | 7.2 |
| 3 | 135 | 21 | H163 | 1 | | 5.1 |
| 3 | 136 | 22 | H051 | 1 | | 3.1 |
| 3 | 137 | 23 | H244 | 1 | | 6.7 |
| 3 | 138 | 24 | H271 | 1 | | 2.6 |
| 3 | 139 | 25 | H006 | 1 | | 4.7 |
| 3 | 140 | 26 | H250 | 1 | | 3.5 |
| 3 | 141 | 27 | H389 | 1 | | 260.0 |
| 3 | 142 | 28 | H302 | 1 | | 2.9 |
| 3 | 143 | 29 | H336 | 1 | | 8.0 |
| 3 | 144 | 30 | H004 | 1 | | 11.8 |
| 3 | 145 | 31 | G619 | 1 | | — |
| | 146 | 32 | D749 | 1 | | 8.7 |
| 3 | 147 | 33 | D761 | 1 | | 6.6 |
| 3 | 148 | 34 | 1 | 1 | | 4.2 |

TABLE 2-continued

Measurement series of serum of patients with prostate carcinoma

| Box 1-4 | ID-No: Sialo | Sample No. | Code | Diagn | Sample volumes | Sialoprotein (ig/L) |
|---|---|---|---|---|---|---|
| 3 | 149 | 35 | 16 | 1 | | 8.5 |
| 3 | 150 | 36 | G969 | 1 | | 27.2 |
| 3 | 151 | 148 | E032 | 6 | | 9.8 |
| 3 | 152 | 149 | E938 | 6 | | 9.4 |
| 3 | 153 | 150 | E674 | 6 | 210iL | 11.5 |
| 3 | 154 | 151 | E890 | 6 | | 10.5 |
| 3 | 155 | 152 | E082 | 6 | | 27.7 |
| 3 | 156 | 153 | E395 | 6 | 210iL | 13.9 |
| 3 | 157 | 154 | E668 | 6 | | 27.9 |
| 3 | 158 | 155 | E242 | 6 | | |
| 3 | 159 | 156 | G320 | 6 | | 7.6 |
| 3 | 160 | 157 | G248 | 6 | | 9.9 |
| 3 | 161 | 158 | G055 | 6 | | 14.5 |
| 3 | 162 | 159 | G034 | 6 | | 5.8 |
| 3 | 163 | 160 | G804 | 6 | | 7.2 |
| 3 | 164 | 161 | G720 | 6 | | 6.2 |
| 3 | 165 | 162 | G774 | 6 | | 10.6 |
| | 166 | 163 | G699 | 6 | | 2.7 |
| 3 | 167 | 164 | G672 | 6 | | 9.0 |
| 3 | 168 | | F776 | 6 | | 15.5 |
| 3 | 169 | 166 | F869 | 6 | | 4.3 |
| 3 | 170 | 167 | H169 | 6 | | 8.9 |
| 3 | 171 | | F199 | 6 | | 13.2 |
| 3 | 172 | 169 | F246 | 6 | | 46.0 |
| 3 | 173 | 170 | F502 | 6 | | 7.4 |
| 3 | 174 | 171 | E806 | 6 | | 7.5 |
| 3 | 175 | 172 | E929 | 6 | | 18.2 |
| 3 | 176 | 173 | E494 | 6 | | 6.7 |
| 3 | 177 | 174 | E758 | 6 | | 6.8 |
| 3 | 178 | 175 | E692 | 6 | | 15.4 |
| 3 | 179 | 176 | G025 | 6 | | 19.3 |
| 3 | 180 | 177 | G723 | 6 | | 16.0 |
| 3 | 181 | 178 | F508 | 6 | | 32.7 |
| 4 | 182 | 179 | G227 | 6 | | 8.1 |
| 4 | 183 | 180 | H261 | 6 | | 23.8 |
| 4 | 184 | 181 | H314 | 6 | | 28.0 |
| 4 | 185 | 294 | H599 | 7 | | — |
| 4 | 186 | 295 | H601 | 7 | | — |
| 4 | 187 | 296 | H737 | 7 | | 7.6 |
| 4 | 188 | 297 | H955 | 7 | | 14.6 |
| 4 | 189 | 298 | H980 | 7 | | 10.0 |
| 4 | 190 | 299 | I010 | 7 | | 3.7 |
| 4 | 191 | 300 | I282 | 7 | | 18.0 |
| 4 | 192 | 301 | 9742(Mü) | 7 | | 42.0 |
| 4 | 193 | 302 | 9773(Mü) | 7 | | 22.3 |
| 4 | 194 | 303 | 9788(Mü) | 7 | | 15.7 |

The diagnosis numbers stand for:
1=healthy men
3=BPH
4=PCa pN0 M0
6=PCa pN1 M0
7=PCa pN1 M1 ossae The pathomorphological classification of the carcinomas was effected in accordance with Van Nuys. M stands for metastases.

TABLE 3 determination of BSP in serum of dialysis patients

| Sample No. | Patient Code | BSP ng/ml Serum | Remark: Apparatus sequence |
|---|---|---|---|
| L50 | G**.E. | 18.8 | 10 Serum > AxSym1(alt): B/10 |
| L69 | H**.R. | 10.1 | 10 Serum > AxSym1(alt): F/07 |
| L85 | W**.D | 77.3 | 10 Serum > HITACHI 917: 5006/1 |
| L131 | K**.E. | 17.1 | 10 Serum > AxSym1(alt): A/09 |
| L13 | B**.M. | 36.6 | 10 Serum > AxSym1(alt): A/04 |
| L14 | H**.L. | 6.6 | 10 Serum > AxSym1(alt): C/04 |
| L15 | P**.B. | 8.1 | 10 Serum > AxSym1(alt): C/02 |
| L16 | S**.I. | 10.4 | 10 Serum > AxSym1(alt): E/09 |
| L24 | H**.A. | 28.1 | 10 Serum > AxSym1(alt): B/04 |
| L38 | B**.M. | 3.1 | 10 Serum > AxSym1(alt): A/03 |
| L41 | K**.C. | 12.5 | 10 Serum > AxSym1(alt): B/02 |
| L50 | H**.L. | 31.9 | 10 Serum > AxSym1(alt): C/03 |
| L77 | W**.P. | 7.8 | 10 Serum > AxSym1(alt): A/04 |
| L84 | D**.K. | 46.9 | 10 Serum > AxSym1(alt): D/08 |
| L88 | M**.H. | 26.5 | 10 Serum > AxSym2(neu): A/01 |
| L134 | S**.M. | 4.2 | 10 Serum > AxSym1(alt): E/04 |
| L73 | H**.K. | 5.2 | 10 Serum > AxSym1(alt): D/01 |
| L75 | L**.I. | 5.5 | 10 Serum > AxSym1(alt): B/05 |
| L78 | Z**.U. | 15.2 | 10 Serum > AxSym1(alt): A/01 |
| L79 | P**.B. | 3.2 | 10 Serum > AxSym1(alt): B/01 |
| L82 | G**.B. | 29.7 | 10 Serum > AxSym1(alt): A/02 |
| L85 | S**.I. | 18.0 | 10 Serum > AxSym1(alt): E/04 |
| L91 | K**.H. | 12.4 | 10 Serum > AxSym1(alt): C/07 |
| L93 | S**.G. | 17.0 | 10 Serum > AxSym1(alt): A/02 |
| L96 | S**.M. | 8.9 | 10 Serum > AxSym1(alt): A/07 |
| L113 | S**.G. | 18.9 | 10 Serum > AxSym1(alt): A/04 |
| L114 | R**.H. | 22.7 | 10 Serum > AxSym1(alt): A/05 |
| L117 | R**.A. | 16.0 | 10 Serum > AxSym1(alt): A/09 |
| L53 | L**.E. | 44.4 | 10 Serum > AxSym1(alt): A/08 |
| L71 | M**.M. | 11.4 | 10 Serum > AxSym1(alt): B/04 |
| L94 | W**.E. | 19.0 | 10 Serum > AxSym1(alt): B/04 |
| L10 | S**.L. | 12.3 | 10 Serum > AxSym1(alt): E/03 |
| L12 | N**.J. | 5.0 | 10 Serum > AxSym1(alt): D/02 |
| L13 | C**.F: | 7.0 | 10 Serum > AxSym1(alt): D/04 |
| L17 | L**.I. | 6.7 | 10 Serum > AxSym1(alt): A/05 |
| L18 | S**.R. | 8.7 | 10 Serum > AxSym1(alt): A/06 |
| L19 | L**.E. | 11.0 | 10 Serum > AxSym1(alt): A/09 |
| L24 | H**.F. | 18.6 | 10 Serum > AxSym1(alt): A/05 |
| L43 | H**.L. | 17.8 | 10 Serum > AxSym1(alt): B/06 |
| L45 | S**.C. | 3.1 | 10 Serum > AxSym1(alt): B/07 |
| L1 | S**.W. | 21.5 | 10 Serum > HITACHI 917: 7002/1 |
| L2 | S**.M. | 14.2 | 10 Serum > HITACHI 917: 7020/2 |
| L3 | S**.A. | 11.8 | 10 Serum > AxSym1(alt): A/02 |
| L4 | D**.J. | 14.4 | 10 Serum > AxSym1(alt): A/01 |
| L5 | G**.H. | 9.0 | 10 Serum > AxSym1(alt): A/02 |
| L6 | B**.U. | 4.7 | 10 Serum > AxSym1(alt): A/03 |
| L7 | S**.L | 8.2 | 10 Serum > AxSym1(alt): A/01 |
| L8 | H**.E. | 15.3 | 10 Serum > AxSym1(alt): A/04 |
| L9 | N**.H. | 7.1 | 10 Serum > AxSym1(alt): E/03 |

An increased BSP value in the serum (>20-25 μg/L) here indicates that a pathological alteration of the bone structure or an increased bone metabolism is present.

The invention claimed is:

1. Purified antibodies that specifically bind epitopes present in human bone sialoprotein (BSP) produced in tumor cells and absent in BSP produced in normal bone cells, wherein the post-translational glycosylation of BSP produced in tumor cells is modified or incomplete in the region of amino acids 120 to 135 of SEQ ID NO: 1 in comparison with the post-translational glycosylation of human BSP produced in normal bone cells, and wherein the epitopes comprise the amino acid sequence TGLAA (SEQ ID NO: 2) or YTGLAA (SEQ ID NO: 3).

2. Antibodies according to claim 1, produced against a peptidic antigen that includes the amino acid sequence TGLAA (SEQ ID NO: 2) or YTGLAA (SEQ ID NO: 3), said peptidic antigen being optionally coupled to a carrier protein.

3. Antibodies according to claim 1 or 2, which are human or humanized.

4. A pharmaceutical composition comprising as active ingredient antibodies according to claim 1 or 2.

5. A method for the determination of bone sialoprotein from tumor cells in body fluids, comprising contacting a sample from said body fluid with antibodies according to claim 1 or 2 and detecting binding of said antibodies to bone sialoprotein from said sample.

6. The method according to claim 5 for the diagnosis and prognosis of bone metastases.

* * * * *

SEQUENCE LISTING

<160> NUMBER OF SEQ ID NOS: 15

<210> SEQ ID NO 1
<211> LENGTH: 317
<212> TYPE: PRT

<213> ORGANISM: Homo sapiens

<400> SEQUENCE: 1

```
Met Lys Thr Ala Leu Ile Leu Ser Ile Leu Gly Met Ala Cys Ala
1               5                   10                  15

Phe Ser Met Lys Asn Leu His Arg Arg Val Lys Ile Glu Asp Ser Glu
            20                  25                  30

Glu Asn Gly Val Phe Lys Tyr Arg Pro Arg Tyr Leu Tyr Lys His
                35                  40                  45

Ala Tyr Phe Tyr Pro His Leu Lys Arg Phe Pro Val Gln Gly Ser Ser
        50                  55                  60

Asp Ser Ser Glu Glu Asn Gly Asp Asp Ser Ser Glu Glu Glu Glu
65                  70                  75                  80

Glu Glu Glu Thr Ser Asn Glu Gly Glu Asn Asn Glu Glu Ser Asn Glu
                85                  90                  95

Asp Glu Asp Ser Glu Ala Glu Asn Thr Thr Leu Ser Ala Thr Thr Leu
            100                 105                 110

Gly Tyr Gly Glu Asp Ala Thr Pro Gly Thr Gly Tyr Thr Gly Leu Ala
                115                 120                 125

Ala Ile Gln Leu Pro Lys Lys Ala Gly Asp Ile Thr Asn Lys Ala Thr
        130                 135                 140

Lys Glu Lys Glu Ser Asp Glu Glu Glu Glu Glu Glu Glu Glu Gly Asn
145                 150                 155                 160

Glu Asn Glu Glu Ser Glu Ala Glu Val Asp Glu Asn Glu Gln Gly Ile
                165                 170                 175

Asn Gly Thr Ser Thr Asn Ser Thr Glu Ala Glu Asn Gly Asn Gly Ser
            180                 185                 190

Ser Gly Gly Asp Asn Gly Glu Gly Glu Glu Ser Val Thr Gly
                195                 200                 205

Ala Asn Ala Glu Gly Thr Thr Glu Thr Gly Gly Gln Gly Lys Gly Thr
        210                 215                 220

Ser Lys Thr Thr Thr Ser Pro Asn Gly Gly Phe Glu Pro Thr Thr Pro
225                 230                 235                 240

Pro Gln Val Tyr Arg Thr Thr Ser Pro Pro Phe Gly Lys Thr Thr Thr
                245                 250                 255

Val Glu Tyr Glu Gly Glu Tyr Glu Tyr Thr Gly Val Asn Glu Tyr Asp
            260                 265                 270

Asn Gly Thr Glu Ile Tyr Glu Ser Glu Asn Gly Glu Pro Arg Gly Asp
                275                 280                 285

Asn Tyr Arg Ala Tyr Glu Asp Glu Tyr Ser Tyr Pro Lys Gly Gln Gly
        290                 295                 300

Tyr Asp Gly Tyr Asp Gly Gln Asn Tyr Tyr His His Gln
305                 310                 315
```

<210> SEQ ID NO 2
<211> LENGTH: 5
<212> TYPE: PRT
<213> ORGANISM: Homo sapiens

<400> SEQUENCE: 2

```
Thr Gly Leu Ala Ala
1               5
```

<210> SEQ ID NO 3
<211> LENGTH: 6
<212> TYPE: PRT

<213> ORGANISM: Homo sapiens

<400> SEQUENCE: 3

Tyr Thr Gly Leu Ala Ala
1               5

<210> SEQ ID NO 4
<211> LENGTH: 12
<212> TYPE: PRT
<213> ORGANISM: Homo sapiens

<400> SEQUENCE: 4

Leu Gly Tyr Gly Glu Asp Ala Thr Pro Gly Thr Gly
1               5                   10

<210> SEQ ID NO 5
<211> LENGTH: 12
<212> TYPE: PRT
<213> ORGANISM: Homo sapiens

<400> SEQUENCE: 5

Glu Thr Gly Gly Gln Gly Lys Gly Thr Ser Lys Thr
1               5                   10

<210> SEQ ID NO 6
<211> LENGTH: 12
<212> TYPE: PRT
<213> ORGANISM: Homo sapiens

<400> SEQUENCE: 6

Phe Lys Gly Gln Gly Tyr Asp Gly Tyr Asp Gly Gln
1               5                   10

<210> SEQ ID NO 7
<211> LENGTH: 15
<212> TYPE: PRT
<213> ORGANISM: Homo sapiens

<400> SEQUENCE: 7

Ile Gln Leu Pro Lys Lys Ala Gly Asp Ile Thr Asn Lys Ala Thr
1               5                   10                  15

<210> SEQ ID NO 8
<211> LENGTH: 15
<212> TYPE: PRT
<213> ORGANISM: Homo sapiens

<400> SEQUENCE: 8

Tyr Thr Gly Leu Ala Ala Ile Gln Leu Pro Lys Lys Ala Gly Asp
1               5                   10                  15

<210> SEQ ID NO 9
<211> LENGTH: 17
<212> TYPE: PRT
<213> ORGANISM: Homo sapiens

<400> SEQUENCE: 9

Gly Asp Ile Thr Asn Lys Ala Thr Lys Glu Lys Glu Lys Glu Ser Asp
1               5                   10                  15
Glu

<210> SEQ ID NO 10
<211> LENGTH: 38
<212> TYPE: PRT

<213> ORGANISM: Homo sapiens

<400> SEQUENCE: 10

Ser Glu Asn Gly Glu Pro Arg Gly Asp Asn Tyr Arg Ala Tyr Glu Asp
1               5                   10                  15

Glu Tyr Ser Tyr Phe Lys Gly Gln Gly Tyr Asp Gly Tyr Asp Gly Gln
            20                  25                  30

Asn Tyr Tyr His His Gln
        35

<210> SEQ ID NO 11
<211> LENGTH: 15
<212> TYPE: PRT
<213> ORGANISM: Homo sapiens

<400> SEQUENCE: 11

Tyr Thr Gly Leu Ala Ala Ile Gln Leu Pro Lys Lys Ala Gly Asp
1               5                   10                  15

<210> SEQ ID NO 12
<211> LENGTH: 18
<212> TYPE: PRT
<213> ORGANISM: Homo sapiens

<400> SEQUENCE: 12

Tyr Glu Ser Glu Asn Gly Glu Pro Arg Gly Asp Asn Tyr Arg Ala Tyr
1               5                   10                  15

Glu Asp

<210> SEQ ID NO 13
<211> LENGTH: 9
<212> TYPE: PRT
<213> ORGANISM: Homo sapiens

<400> SEQUENCE: 13

Leu Lys Arg Phe Pro Val Gln Gly Gly
1               5

<210> SEQ ID NO 14
<211> LENGTH: 34
<212> TYPE: DNA
<213> ORGANISM: Homo sapiens

<400> SEQUENCE: 14
gccgctagcc cttctcaatg aaaaatttgc atcg                                34

<210> SEQ ID NO 15
<211> LENGTH: 38
<212> TYPE: DNA
<213> ORGANISM: Homo sapiens

<400> SEQUENCE: 15
caatgactgc ggccgctcac tggtggtggt agtaattc                            38